United States Patent [19]

Hansen et al.

[11] Patent Number: 5,100,895

[45] Date of Patent: Mar. 31, 1992

[54] HETEROCYCLIC COMPOUNDS AND THEIR PREPARATION AND USE

[75] Inventors: Holger C. Hansen, Vaerlose; Marit Kristiansen, Soborg, both of Denmark

[73] Assignee: Novo Nordisk A/S, Bagsvaerd, Denmark

[21] Appl. No.: 578,054

[22] Filed: Sep. 5, 1990

[30] Foreign Application Priority Data

Sep. 8, 1989 [DK] Denmark .............................. 4435/89

[51] Int. Cl.$^5$ .................. A61K 31/505; C07D 239/06
[52] U.S. Cl. ..................................... 514/257; 544/247
[58] Field of Search ......................... 544/247; 514/257

[56] References Cited

U.S. PATENT DOCUMENTS 3,847,918 11/1974 Kathawala ........................... 544/247
4,774,245 9/1988 Watgen et al. ....................... 544/343

FOREIGN PATENT DOCUMENTS 0307814 3/1989 European Pat. Off. ............ 544/247

Primary Examiner—Mukund J. Shah
Assistant Examiner—Y. N. Gupta
Attorney, Agent, or Firm—Steve T. Zelson; Elias J. Lambiris

[57] ABSTRACT

New imidazoquinazoline compounds having the general formula

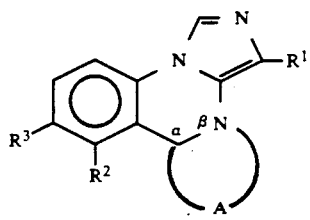

wherein

A together with the α-marked carbon atom and the β-marked nitrogen atom is one of the groups

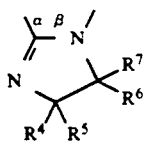

a

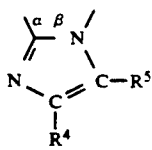

b

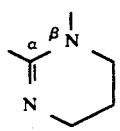

c wherein $R^4$, $R^5$, $R^6$ and $R^7$ independently are hydrogen, halogen $C_{1-6}$-alkyl, aryl or aralkyl $R^1$ is

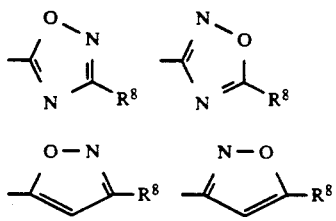

cyano or $CO_2R^8$, wherein $R^8$ is hydrogen, $C_{1-6}$-alkyl or $C_{3-7}$-cycloalkyl, trifluoromethyl or $C_{1-6}$-alkoxymethyl, $R^2$ and $R^3$ independently are hydrogen, halogen, CN, $C_{1-6}$-alkyl, $C_{2-6}$-alkenyl, $C_{2-6}$-alkynyl, trifluoromethyl, $C_{1-6}$-alkoxy, dialkylaminoalkoxy, aralkoxy, aryloxy which may be substituted with halogen or alkoxy, a cyclic amino group, or $NR^9R^{10}$, wherein $R^9$ and $R^{10}$ independently are hydrogen or $C_{1-6}$-alkyl.

The compounds are useful in psychopharmaceutical preparations as anticonvusants, anxiolytics, hypnotics, antipsychotics, antiemetics, or in improving the cognitive function of the brain of mammals.

10 Claims, No Drawings

HETEROCYCLIC COMPOUNDS AND THEIR PREPARATION AND USE

The present invention relates to therapeutically active tetracyclic imidazoquinazoline compounds, a method of preparing the same, pharmaceutical compositions comprising the compounds, and to methods of treating therewith. The novel compounds are useful in psychopharmaceutical applications, e.g., in the treatment of central nervous system ailments, for example, as anticonvulsants, anxiolytics, hypnotics, antipsychotics, antiemetics, or in improving the cognitive function of the brain of mammals.

It is well known (Squires, R. F. and Braestrup, C. in Nature (London) 266 (1977) 732-734) that specific sites in the central nervous systems of vertebrates exhibit a high specific affinity for binding 1,4- and 1,5-benzodiazepines. These sites are called benzodiazepine receptors.

It has now been found that members of a novel group of tetracyclic imidazoquinazoline compounds have strong affinity for the benzodiazepine receptors which make them useful in psychopharmaceutical preparations.

Accordingly, it is an object of the invention to provide such novel tetracyclic imidazoquinazoline compounds.

The compounds of the invention have the general formula I

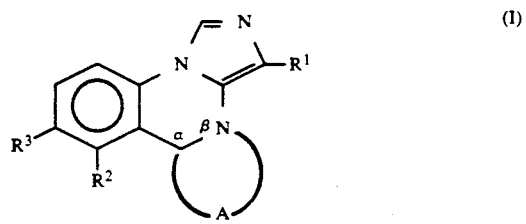

and pharmaceutically acceptable acid addition salts thereof, wherein
A together with the α-marked carbon atom and the β-marked nitrogen atom is one of the groups a

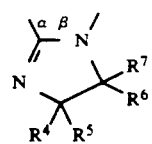

b

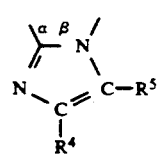

c

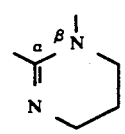

wherein $R^4$, $R^5$, $R^6$ and $R^7$ independently are hydrogen, halogen, $C_{1-6}$-alkyl, aryl, or aralkyl;

$R^1$ is

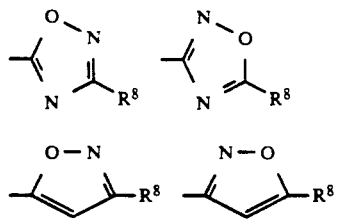

cyano or $CO_2R^8$, wherein $R^8$ is hydrogen, $C_{1-6}$-alkyl or $C_{3-7}$-cycloalkyl, trifluoromethyl or $C_{1-6}$-alkoxymethyl, $R^2$ and $R^3$ independently are hydrogen, halogen, CN, $C_{1-6}$-alkyl, $C_{2-6}$-alkenyl, $C_{2-6}$-alkynyl, trifluoromethyl, $C_{1-6}$-alkoxy, dialkylaminoalkoxy, aralkoxy, aryloxy which may be substituted with halogen or alkoxy, a cyclic amino group, or $NR^9R^{10}$, wherein $R^9$ and $R^{10}$ independently are hydrogen or $C_{1-6}$-alkyl.

The invention also relates to methods of preparing the above mentioned compounds. These methods comprise:

a) reacting a compound of formula II

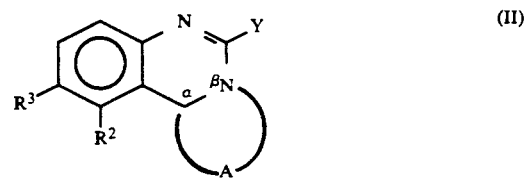 (II)

wherein A, $R^2$ and $R^3$ are as defined above and wherein Y is a leaving group, with a compound having the formula III $$CN-CH_2-R^1 \qquad (III)$$

wherein $R^1$ is as defined above, to form a compound of the invention, or b) reacting a reactive derivative of a compound having the general formula IV

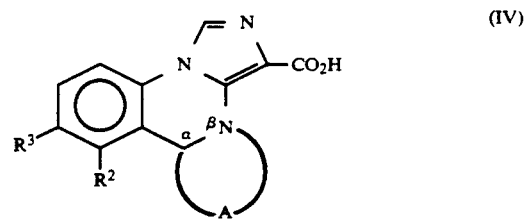 (IV)

wherein A, $R^2$ and $R^3$ are as defined above with a compound having the general formula V $$R^8-C(=NOH)NH_2 \qquad (V)$$

wherein $R^8$ is as defined above to form a compound of the general formula I wherein $R^1$ is

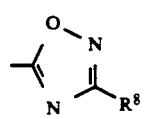

wherein $R^8$ is as defined above, or c) reacting a compound of the general formula VI

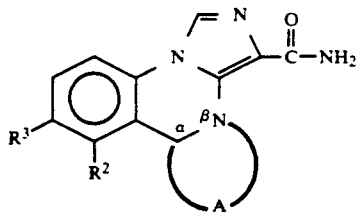

wherein —A—, $R^2$ and $R^3$ have the meanings set forth above, with a dehydrating agent to form a compound of formula I, wherein —A—, $R^2$ and $R^3$ have the meanings set forth above and wherein $R^1$ is cyano, or d) reacting a compound of formula VII

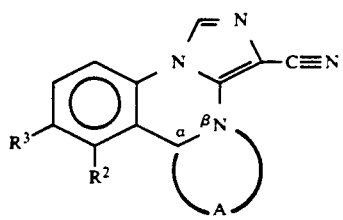

wherein —A—, $R^2$ and $R^3$ have the meaning set forth above, with $NH_2OH$ to form a compound of formula VIII

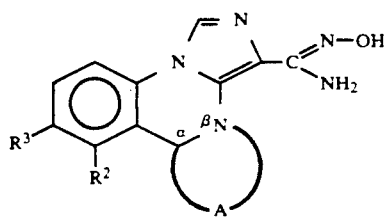

wherein —A—, $R^2$, and $R^3$ have the meanings set forth above, and reacting the compound of formula VIII with $R^8$—COCl or with $(R^8CO)_2O$, wherein $R^8$ is as defined above to form a compound of the general formula I wherein $R^1$ is

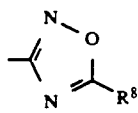

wherein $R^8$ is as defined above, or e) reacting a compound of formula I wherein $R^1$, $R^2$, and $R^3$ are as defined above, and —A— together with the α-marked carbon atom and the β-marked nitrogen atom is

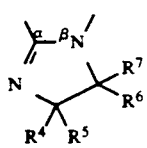

wherein $R^5$ and $R^6$ are vicinal hydrogen atoms, with an oxidizing agent to form a compound of the general formula I wherein

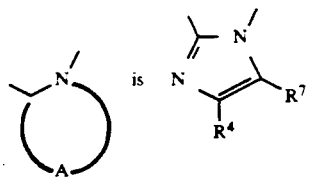

wherein $R^4$ and $R^7$ are as defined above, or f) reacting a compound of the general formula I, wherein —A—, $R^1$, and $R^3$ are as defined above and $R^2$ is halogen, with an alcohol, a phenol, or an amine, to form a compound of formula I, wherein $R^2$ is an $C_{1-6}$-alkoxy, aryloxy, aralkoxy, cycloalkoxy, or amino group which may all be substituted, or g) reacting a compound of formula IX

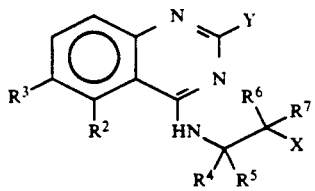

wherein Y, $R^2$, $R^3$, $R^4$, $R^5$, $R^6$ and $R^7$ are as defined above, and X is a leaving group, e.g. halogen, with a compound of formula III, to form a compound of formula I.

The leaving group, Y, may be any suitable leaving group and, for example, those disclosed in U.S. Pat. Nos. 4,031,079 or 4,359,420, for example, halogen, alkylthio, e.g., methylthio, aralkylthio, N-nitrosoalkylamino, alkoxy, mercapto, —OP(O)(OR)$_2$ wherein R is lower-alkyl or —OP(O)(NR'R")$_2$ wherein R' and R" each represents lower-alkyl or phenyl, or together with the nitrogen atom to which they are attached represent a heterocyclic radical such as morpholino, pyrrolidino, piperidino, or methylpiperazino. The reaction is preferably carried out under alkaline conditions, i.e., in the presence of a base, and among bases alkali metal (e.g., potassium or sodium) alkoxides or hydrides are preferred. The reaction is preferably conducted in the presence of an organic solvent which is nonreactive with the reactants and products of reaction under the conditions of reaction, especially an anhydrous solvent and preferably an anhydrous aprotic solvent such as dimethylformamide (DMF), tetrahydrofuran (THF), or the like. The temperature range employed may be any range suitable for the reaction to proceed at a reasonable rate and without undue delay or decomposition and a range from a minus forty (—40) degrees Celsius to about room temperature is accordingly usually particularly suitable.

The starting materials employed in the syntheses of the compounds of formula I are either known or may be prepared in conventional manner from available materials. Thus, the compounds of formula II may be produced by annellation of 4-chloroquinazolines, for example, by procedures similar to those of F. Claudi et al., J. Org. Chem. 39, 3508 (1974); R. S. Sinyak, I. A. Mazur, Farm. Zh. (Kiev) 30, 29 (1975), (Chem. Abstr. 83, 97198); G. E. Hardtmann et al., J. Med. Chem. 18, 447 (1975). Imidazo[1,2-c]quinazolines may also be produced by annellation of 4-aminoquinazolines, e.g. as described by A. Guiffer et al., J. Heterocycl. Chem. 27, 421 (1990), or by a double annellation of anthranilonitriles according to E. P. Papadopoulos, J. Heterocycl. Chem. 18, 515 (1981); idem, 17, 1553 (1980). 2,3-Dihydroimidazo[1,2-c]quinazolines may be oxidized to give the 2,3-unsaturated analogs, preferentially by oxidation with nickel peroxide in an inert solvent.

The isocyanomethyloxadiazoles of formula III may be prepared as described in the prior art, e.g. U.S. Pat. No. 4,774,245. 3(5)-Alkyl-5(3)-halomethylisoxazoles, either known or prepared from appropriate starting materials according to known procedures (e.g. U.S. 3,290,301 and Ger. Offen. DE 25 49 962), may by conventional techniques be converted to 3(5)-alkyl-5(3)-aminomethylisoxazoles which in turn may be N-formylated and subsequently dehydrated to give isocyanomethylisoxazoles.

The pharmaceutical properties of the compounds of the invention can be illustrated by determining their capability for displacing radioactive labelled flunitrazepam from benzodiazepine receptors.

The displacement activity of the compounds of the invention may be found by determining the $ED_{50}$ value. The $ED_{50}$ value represents the dose (mg/kg) of a test substance which causes the specific binding of $^3$H-flunitrazepam to benzodiazepine receptors in a living brain to be reduced to 50% of the control value.

Such an in vivo test is carried out as described in U.S. Pat. No. 4,774,245.

Test results obtained by testing some compounds of the invention will appear from the following table I.

TABLE I

| Compound | $ED_{50}$ (mg/kg) |
|---|---|
| 6 | 0.23 |
| 1 | 0.47 |
| 7 | 0.92 |
| 8 | 1.7 |
| 12 | 0.08 |
| 19 | 0.08 |
| 28 | 0.12 |
| 21 | 0.26 |

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one tenth (0.1) milligram of active ingredient or, more broadly, one tenth (0.1) to hundred (100) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional method of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxilliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compounds of the invention are dispensed in unit dosage form comprising 0.05-100 mg in a pharmaceutically-acceptable carrier per unit dosage.

A typical tablet which may be prepared by conventional tabletting techniques contains:

| Active compound | 1.0 mg |
|---|---|
| Lactosum | 67.8 mg Ph. Eur. |
| Avicel ® | 31.4 mg |
| Amberlite ® IRP 88 | 1.0 mg |
| Magnesii stearas | 0.25 mg Ph. Eur. |

Due to their high degree of affinity for the benzodiazepin receptors, the compounds of the invention are extremely useful in the treatment of central nervous system ailments or disorders, when administered in an amount effective for the alleviation, amelioration, or elimination thereof. The important CNS activity of the compounds of the invention includes both anticonvulsant, hypnotic, nootropic and anxiolytic activities along with a low toxicity, together presenting a most favorable therapeutic index. The compounds of the invention may accordingly be administered to a subject, e.g., a living mammal body, including a human, in need of the same for the treatment, alleviation, amelioration, or elimination of an indication, associated with the central nervous system and the socalled benzodiazepine receptors, which requires such psychopharmaceutical treatment, e.g., especially convulsion, insomnia, anxiety and/or dementia states, if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g., an anticonvulsant and/or anxiolytic amount, and in any event an amount which is effective for the alleviation of such a central nervous system ailment due to their benzodiazepine receptor affinity. Suitable dosage ranges are 1–200 milligrams daily, 1–100 milligrams daily, and especially 1–30 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples, which may not be construed as limiting:

EXAMPLE 1

5-(5-cyclopropyl-1,2,4-oxadiazol-3-yl)-2,3-dihydrodiimidazol[1,5-a:1',2'-c]quinazoline (Compound 1)

Method A

To a stirred mixture of 5-chloro-2,3-dihydroimidazol[1,2-c]quinazoline (4.3 g, 21 mmol) and 5-cyclopropyl-3-isocyanomethyl-1,2,4-oxadiazole (4.1 g, 27 mmol) in dry DMF (100 ml) under nitrogen at room temperature was added solid potassium t-butoxide (3.1 g, 27 mmol). After stirring for 1 h the solvent was evaporated in vacuo and the residue treated with a mixture of water (100 ml) and ethyl acetate (25 ml). The precipitated title compound was collected by filtration and dried to give pale crystals, m.p. 200°–202° C.

Method B

To a stirred suspension of 2,3-dihydroimidazo[1,2-c]quinazolin-5-ol (0.94 g, 5 mmol) in dry DMF (50 ml) under nitrogen was added 60% sodium hydride dispersion in mineral oil (0.26 g, 6.5 mmol) at ambient temperature. After 10 min. diethyl chlorophosphate (0.9 ml, 6.5 mmol) was added, and stirring was continued for 1 h. The resulting solution was charged with a −30° C. cold, freshly prepared solution of 5-cyclopropyl-3-isocyanomethyl-1,2,4-oxadiazole (0.97 g, 6.5 mmol) and potassium t-butoxide (0.73 g, 6.5 mmol) in dry DMF (10 ml). The mixture was stirred for 1.5 h at room temperature and then the solvent was evaporated in vacuo. The residue was triturated with a mixture of water (10 ml) and ethyl acetate (5 ml). The resulting precipitate was partitioned between dichloromethane (75 ml) and 2M sodium hydroxide (30 ml). The organic phase was dried and evaporated, and the residue was brought to crystallize upon treatment with water/ethyl acetate. The crystals were filtered off, dried and recrystallized from isopropyl alcohol to give the title compound. M.p. 204°–205° C.

In a similar manner the following compounds were prepared:

5-(3-cyclopropyl-1,2,4-oxadiazol-5-yl)-2,3-dihydrodiimidazo[1,5-a:1',2'-c]quinazoline, m.p. 237°–40° C., from 5-chloro-2,3-dihydroimidazo[1,2-c]quinazoline and 3-cyclopropyl-5-isocyanomethyl-1,2,4-oxadiazole. (Compound 2).

ethyl 2,3-dihydrodiimidazo[1,5-a:1',2'-c]quinazoline-5-carboxylate, m.p. 258°–60° C., from 5-chloro-2,3-dihydroimidazo[1,2-c]quinazoline and ethyl isocyanoacetate. (Compound 3).

Tert-butyl 2,3-dihydrodiimidazo[1,5-a:1',2'-c]quinazoline-5-carboxylate, m.p. 202°–5° C., from 5-chloro-2,3-dihydroimidazo[1,2-c]quinazoline and tert-butyl isocyanoacetate.

12-Chloro-2,3-dihydro-5-(5-methyl-1,2,4-oxadiazol-3-yl)diimidazo[1,5-a:1',2'-c]quinazoline, m.p. 235°–37° C., from 5,10-dichloro-2,3-dihydroimidazo[1,2-c]quinazoline and 3-isocyanomethyl-5-methyl-1,2,4-oxadiazole. (Compound 5).

12-Chloro-5-(5-cyclopropyl-1,2,4-oxadiazol-3-yl)-2,3-dihydrodiimidazo[1,5-a:1',2'-c]quinazoline, m.p. 242°–243° C., from 5,10-dichloro-2,3-dihydroimidazo[1,2-c]quinazoline and 5-cyclopropyl-3-isocyanomethyl-1,2,4-oxadiazole. (Compound 6).

12-Bromo-5-(5-cyclopropyl-1,2,4-oxadiazol-3-yl)-2,3-dihydroiimidazo[1,5-a:1',2'-c]quinazoline, m.p. 228°–30° C., from 10-bromo-5-chloro-2,3-dihydroimidazo[1,2-c]quinazoline and 5-cyclopropyl-3-isocyanomethyl-1,2,4-oxadiazole. (Compound 7).

12-Bromo-5-(3-cyclopropyl-1,2,4-oxadiazol-5-yl)-2,3-dihydrodiimidazo[1,5-a:1',2'-c]quinazoline, m.p. 278°–81° C., from 10-bromo-5-chloro-2,3-dihydroimidazo[1,2-c]quinazoline and 3-cyclopropyl-5-isocyanomethyl-1,2,4-oxadiazole.

5-(5-Cyclopropyl-1,2,4-oxadiazol-3-yl)diimidazo[1,5-a:1',2'-c]quinazoline, m.p. 238°–40° C., from 5-chloroimidazo[1,2-c]quinazoline and 5-cyclopropyl-3-isocyanomethyl-1,2,4-oxadiazole. (Compound 9).

6-(5-Cyclopropyl-1,2,4-oxadiazol-3-yl)-3,4-dihydro-2H-imidazo[1,5-a]pyrimido[1,2-c]quinazoline, m.p. 174°–176° C., from 6-chloro-3,4-dihydro-2H-pyrimido[1,2-c]quinazoline and 5-cyclopropyl-3-isocyanomethyl-1,2,4-oxadiazole. (Compound 10).

2,3-Dihydro-5-(3-methyl-5-isoxazolyl)diimidazo[1,5-a:1',2'-c]quinazoline, m.p. 290°–292° C., from 5-chloro-2,3-dihydroimidazo[1,2-c]quinazoline and 5-isocyanomethyl-3-methylisoxazole. (Compound 11).

5-(5-Cyclopropyl-1,2,4-oxadiazol-3-yl)-2,3-dihydro-12-trifluoromethyldiimidazo[1,5-a:1',2'-c]quinazoline, m.p. 229°–230° C., from 5-chloro-2,3-dihydro-10-trifluoromethylimidazo[1,2-c]quinazoline and 5-cyclopropyl-3-isocyanomethyl-1,2,4-oxadiazole. (Compound 12).

5-(5-Cyclopropyl-1,2,4-oxadiazol-3-yl)-12-fluoro-2,3-dihydrodiimidazo[1,5-a:1',2'-c]quinazoline, m.p. 220°–223° C., from 5-chloro-10-fluoro-2,3-dihydroimidazo[1,2-c]quinazoline and 5-cyclopropyl-3-isocyanomethyl-1,2,4-oxadiazole. (Compound 13).

5-(3-Cyclopropyl-1,2,4-oxadiazol-5-yl)diimidazo[1,5-a:1',2'-c]quinazoline, m.p. 259°–260° C., from 5-chloroimidazo[1,2-c]quinazoline and 3-cyclopropyl-5-isocyanomethyl-1,2,4-oxadiazole (Compound 14).

12-Chloro-5-(3-cyclopropyl-1,2,4-oxadiazol-5-yl)-2,3-dihydrodiimidazo[1,5-a:1',2'-c]quinazoline, m.p. 278°–280° C., from 5,10-dichloro-2,3-dihydroimidazo[1,2-c]quinazoline and 3-cyclopropyl-5-isocyanomethyl-1,2,4-oxadiazole. (Compound 15).

12-Chloro-5-(5-cyclopropyl-1,2,4-oxadiazol-3-yl)-2,3-dihydro-3-phenyldiimidazo[1,5-a:1',2'-c]quinazoline, m.p. 141°–45° C., from 5,10-dichloro-2,3-dihydro-3-phenylimidazo[1,2-c]quinazoline and 5-cyclopropyl-3-isocyanomethyl-1,2,4-oxadiazole. (Compound 16).

12-Chloro-5-(5-cyclopropyl-1,2,4-oxadiazol-3-yl)-2,3-dihydro-2-methyldiimidazo[1,5-a:1',2'-c]quinazoline, m.p. 227°–230° C., from 5,10-dichloro-2,3-dihydro-2-methylimidazo[1,2-c]quinazoline and 5-cyclopropyl-3-isocyanomethyl-1,2,4-oxadiazole. (Compound 17).

12-Chloro-5-(5-cyclopropyl-1,2,4-oxadiazol-3-yl)diimidazo[1,5-a:1',2'-c]quinazoline, m.p. 246°-247° C., from 5,10-dichloroimidazo[1,2-c]quinazoline and 5-cyclopropyl-3-isocyanomethyl-1,2,4-oxadiazole. (Compound 18).

5-(3-Cyclopropyl-1,2,4-oxadiazol-5-yl)-2,3-dihydro-12-trifluoromethyldiimidazo[1,5-a:1',2'-c]quinazoline, m.p. 259°-260° C., from 5-chloro-2,3-dihydro-10-trifluoromethylimidazo[1,2-c]quinazoline and 3-cyclopropyl-5-isocyanomethyl-1,2,4-oxadiazole. (Compound 19).

12-Chloro-5-(5-cyclopropyl-1,2,4-oxadiazol-3-yl)-2,3-dihydro-3-methyldiimidazo[1,5-a:1',2'-c]quinazoline, m.p. 241°-243° C., from 5,10-dichloro-2,3-dihydro-3-methylimidazo[1,2-c]quinazoline and 5-cyclopropyl-3-isocyanomethyl-1,2,4-oxadiazole. (Compound 20).

5-(5-Cyclopropyl-1,2,4-oxadiazol-3-yl)-11-fluoro-2,3-dihydrodiimidazo[1,5-a:1',2'-c]quinazoline, m.p. 215°-216° C., from 5-chloro-9-fluoro-2,3-dihydroimidazo[1,2-c]quinazoline and 5-cyclopropyl-3-isocyanomethyl-1,2,4-oxadiazole. (Compound 21).

5-(3-Cyclopropyl-1,2,4-oxadiazol-5-yl)-11-fluoro-2,3-dihydrodiimidazo[1,5-a:1',2'-c]quinazoline, m.p. 305°-310° C., from 5-chloro-9-fluoro-2,3-dihydroimidazo[1,2-c]quinazoline and 3-cyclopropyl-5-isocyanomethyl-1,2,4-oxadiazole. (Compound 22).

5-(5-Cyclopropyl-1,2,4-oxadiazol-3-yl)-12-methoxy-2,3-dihydrodiimidazo[1,5-a:1',2'-c]quinazoline, m.p. 207°-208° C., from 5-chloro-2,3-dihydro-10-methoxyimidazo[1,2-c]quinazoline and 5-cyclopropyl-3-isocyanomethyl-1,2,4-oxadiazole. (Compound 23).

5-(3-Cyclopropyl-1,2,4-oxadiazol-5-yl)-12-methoxy-2,3-dihydrodiimidazo[1,5-a:1',2'-c]quinazoline, m.p. 230°-232° C., from 5-chloro-2,3-dihydro-10-methoxyimidazo[1,2-c]quinazoline and 3-cyclopropyl-5-isocyanomethyl-1,2,4-oxadiazole. (Compound 24).

11-Chloro-5-(5-cyclopropyl-1,2,4-oxadiazol-3-yl)-2,3-dihydrodiimidazo[1,5-a:1',2'-c]quinazoline, m.p. 203°-205° C., from 5,9-dichloro-2,3-dihydroimidazo[1,2-c]quinazoline and 5-cyclopropyl-3-isocyanomethyl-1,2,4-oxadiazole. (Compound 25).

12-Chloro-2,3-dihydro-5-(3-methyl-isoxazol-5-yl)diimidazo[1,5-a:1',2'-c]quinazoline, m.p. 297°-299° C., from 5,10-dichloro-2,3-dihydroimidazo[1,2-c]quinazoline and 5-isocyanomethyl-3-methylisoxazole. (Compound 26).

12-Bromo-5-(5-cyclopropyl-1,2,4-oxadiazol-3-yl)diimidazo[1,5-a:1',2'-c]quinazoline, m.p. 250°-251° C., from 10-bromo-5-chloroimidazo[1,2-c]quinazoline and 5-cyclopropyl-3-isocyanomethyl-1,2,4-oxadiazole. (Compound 27).

5-(5-Cyclopropyl-1,2,4-oxadiazol-3-yl)-12-trifluoromethyldiimidazo[1,5-a:1',2'-c]quinazoline, m.p. 252°-253° C., from 10-trifluoromethylimidazo[1,2-c]quinazoline and 5-cyclopropyl-3-isocyanomethyl-1,2,4-oxadiazole. (Compound 28).

S(−)-12-chloro-5-(5-cyclopropyl-1,2,4-oxadiazol-3-yl)-2,3-dihydro-2-methyldiimidazo[1,5-a:1',2'-c]quinazoline, m.p. 242°-243° C., from S(−)-5,10-dichloro-2,3-dihydro-2-methylimidazo[1,2-c]quinazoline and 5-cyclopropyl-3-isocyanomethyl-1,2,4-oxadiazole. (Compound 29).

5-(3-Cyclopropyl-1,2,4-oxadiazol-5-yl)-12-fluoro-2,3-dihydrodiimidazo[1,5-a:1',2'-c]quinazoline, m.p. 229°-231° C., from 5-chloro-10-fluoro-2,3-dihydroimidazo[1,2-c]quinazoline and 3-cyclopropyl-5-isocyanomethyl-1,2,4-oxadiazole. (Compound 30).

11-Chloro-5-(3-cyclopropyl-1,2,4-oxadiazol-5-yl)-2,3-dihydrodiimidazo[1,5-a:1',2'-c]quinazoline, m.p. 277°-278° C., from 5,9-dichloro-2,3-dihydroimidazo[1,2-c]quinazoline and 3-cyclopropyl-5-isocyanomethyl-1,2,4-oxadiazole. (Compound 31).

12-Bromo-5-(3-cyclopropyl-1,2,4-oxadiazol-5-yl)diimidazo[1,5-a:1',2'-c]quinazoline, m.p. 277°-279° C., from 10-bromo-5-chloro-imidazo[1,2-c]quinazoline and 3-cyclopropyl-5-isocyanomethyl-1,2,4-oxadiazole. (Compound 32).

12-Chloro-5-(3-cyclopropyl-1,2,4-oxadiazol-5-yl)diimidazo[1,5-a:1',2'-c]quinazoline, m.p. 281°-281° C., from 5,10-dichloroimidazo[1,2-c]quinazoline and 3-cyclopropyl-5-isocyanomethyl-1,2,4-oxadiazole. (Compound 33).

R(+)-12-chloro-5-(cyclopropyl-1,2,4-oxadiazol-3-yl)-2,3-dihydro-2-methyldiimidazo[1,5-a:1',2'-c]quinazoline, m.p. 243°-244° C., from R(+)-5,10-dichloro-2,3-dihydro-2-methylimidazo[1,2-c]quinazoline and 5-cyclopropyl-3-isocyanomethyl-1,2,4-oxadiazole. (Compound 34).

2-Chloro-5-(5-cyclopropyl-1,2,4-oxadiazol-3-yl)-12-fluorodiimidazo[1,5-a:1',2'-c]quinazoline, m.p. 270°-273° C. from 2,5-dichloro-10-fluoroimidazo[1,2-c]quinazoline and 5-cyclopropyl-3-isocyanomethyl-1,2,4-oxadiazole. (Compound 35).

5-(3-Cyclopropyl-1,2,4-oxadiazol-5-yl)-11-fluorodiimidazo[1,5-a:1',2'-c]quinazoline, m.p. 312°-314° C. (dec.), from 5-chloro-9-fluoroimidazo[1,2-c]quinazoline and 3-cyclopropyl-5-isocyanomethyl-1,2,4-oxadiazole. (Compound 36).

5-(5-Cyclopropyl-1,2,4-oxadiazol-3-yl)-11-fluorodiimidazo[1,5-a:1',2'-c]quinazoline, m.p. 261°-263° C., from 5-chloro-9-fluoroimidazo[1,2-c]quinazoline and 5-cyclopropyl-3-isocyanomethyl-1,2,4-oxadiazole. (Compound 37).

EXAMPLE 2

5-(3-Cyclopropyl-1,2,4-oxadiazol-5-yl)-12-fluorodiimidazo[1,5-a:1',2'-c]quinazoline A mixture of 5-(3-cyclopropyl-1,2,4-oxadiazol-5-yl)-12-fluoro-2,3-dihydrodiimidazo[1,5-a:1',2'-c]quinazoline (2.0 g, 5.9 mmol), nickel peroxide (10 g), and benzene (125 ml) was heated at reflux for 3.5 hours, cooled slightly, and filtered. The filtrate was evaporated to give the title compound as light yellow crystals, m.p. 266°-268° C. (Compound 38).

In a similar manner the following compounds were prepared from the appropriate 2,3-dihydro compounds:

5-(5-Cyclopropyl-1,2,4-oxadiazol-3-yl)-12-fluorodiimidazo[1,5-a:1',2'-c]quinazoline, m.p. 239°-240° C. (Compound 39).

12-Chloro-5-(5-cyclopropyl-1,2,4-oxadiazol-3-yl)-2-methyldiimidazo[1,5-a:1',2'-c]quinazoline, m.p. 212°-213° C. (Compound 40).

5-(5-Cyclopropyl-1,2,4-oxadiazol-3-yl)-12-trifluoromethyldiimidazo[1,5-a:1',2'-c]quinazoline, m.p. 252°-253° C. (Compound 28).

12-Chloro-5-(5-cyclopropyl-1,2,4-oxadiazol-3-yl)diimidazo[1,5-a:1',2'-c]quinazoline, m.p. 246°-247° C. (Compound 18).

EXAMPLE 3

5-(5-Cyclopropyl-1,2,4-oxadiazol-3-yl)-2,3-dihydrodiimidazo[1,5-a:1',2'-c]quinazoline hydrogen L-tartrate Equimolar amounts of 5-(5-cyclopropyl-1,2,4-oxadiazol-3-yl)-2,3-dihydrodiimidazo[1,5-a:1',2'-c]quinazoline (0.64 g) and L-tartaric acid (0.30 g) was stirred in dichloromethane (25 ml) until a clear solution was obtained. The solvent was removed by evaporation in vacuo and the residue was triturated with isopropyl alcohol. The crystalline precipitate was filtered off and recrystallized from ethanol yielding the title compound as pale crystals, m.p. 160°-163° C. (Compound 41).

EXAMPLE 4

12-Chloro-5-(5-cyclopropyl-1,2,4-oxadiazol-3-yl)-2,3-dihydro-2,2-dimethyldiimidazo[1,5-a:1',2'-c]quinazoline A mixture of 2,5-dichloro-4-(1,1-dimethyl-2-hydroxyethylamino)quinazoline (6.6 g, 23 mmol), dichloromethane (125 ml) and thionyl chloride (3 ml, 41 mmol) was stirred for 1.5 hours at RT and filtered. The filter cake was partioned between dichloromethane (100 ml) and water (100 ml), 25% aqueous ammonia was added until pH = 8-9. The organic layer was dried over magnesium sulphate and evaporated. The residue of crystalline 2,5-dichloro-4-(2-chloro-1,1-dimethylaminomethyl)quinazoline, m.p. 125°-126° C., was used without further purification.

To a stirred mixture of 2,5-dichloro-4-(2-chloro-1,1-dimethylaminomethyl)quinazoline (1.5 g, 4.9 mmol) and 5-cyclopropyl-3-isocyanomethyl-1,2,4-oxadiazole (1.1 g, 7.4 mmol) in dry DMF (20 ml) was added solid potassium t-butoxide (0.9, 8 mmol) under nitrogen and at 5°-10° C. The mixture was stirred at room temperature for 1 h. The precipitated title compound was collected by filtration, washed with water (10 ml) and acetone (6 ml), and dried to give beige crystals, m.p. 239°-240° C. (Compound 42).

EXAMPLE 5

10-Bromo-5-chloro-2,3-dihydroimidazo[1,2-c]quinazoline

A suspension of 5-bromo-2-chloro-4-(2-hydroxyethylamino)quinazoline (2.3 g, 7.6 mmol) in phosphorus oxychloride (POCl$_3$) (60 ml) was heated at reflux for 5 h. The excess of POCl$_3$ was evaporated and the residue partioned between dichloromethane (50 ml) and 1M aqueous sodium hydroxide (50 ml). The organic layer was washed with water (25 ml), dried over sodium sulphate and evaporated. The residue was triturated with ether (25 ml) and the precipitate collected by filtration to give the title compound as colourless crystals, m.p. 220°-23° C.

In the same manner the following compounds were prepared:

5,10-Dichloro-2,3-dihydroimidazo[1,2-c]quinazoline, m.p. 231°-34° C., from 2,5-dichloro-4-(2-hydroxyethylamino)quinazoline.

5-Chloro-2,3-dihydroimidazo[1,2-c]quinazoline, m.p. 205°-209° C., from 2-chloro-4-(2-hydroxyethylamino)quinazoline.

6-Chloro-3,4-dihydro-2H-pyrimido[1,2-c]quinazoline, m.p. 307°-308° C., from 2-chloro-4-(3-hydroxypropylamino)quinazoline.

5-Chloro-2,3-dihydro-10-trifluoromethylimidazo[1,2-c]quinazoline, m.p. 212°-216° C., from 2-chloro-4-(2-hydroxyethylamino)-5-trifluoromethylquinazoline.

EXAMPLE 6

S(−)-5,10-dichloro-2,3-dihydro-2-methylimidazo[1,2-c]quinazoline

A mixture of S-2,5-dichloro-4-(2-hydroxy-1-methylethylamino)quinazoline (8.0 g, 29.4 mmol), dichloromethane (180 ml) and thionyl chloride (3.6 ml, 49.6 mmol) was stirred for 1 hour at room temperature. The mixture was evaporated to dryness and the residue resolved in acetone (350 ml). Potassium carbonate (35 g) and potassium iodide (0.5 g) were added and the mixture was heated at reflux for 5 hours. After cooling to room temperature the mixture was filtered and the filtrate evaporated to dryness. The residue was treated with a mixture of water (30 ml) and ether (10 ml) to give the title compound a crystalline precipitate, which was filtered off and dried, m.p. 161°-164° C.

$[\alpha]_D^{20} = -60.6$ (c = 2; 50% acetic acid in methanol)

In the same manner the following compounds were obtained:

R(+)-5,10-dichloro-2,3-dihydro-2-methylimidazo[1,2-c]quinazoline, m.p. 151°-162° C. from R-2,5-dichloro-4-(2-hydroxy-1-methylethylamino)quinazoline.

5,10-Dichloro-2,3-dihydro-3-phenylimidazo[1,2-c]quinazoline, m.p. 135°-143° C., from 2,5-dichloro-4-(2-hydroxy-2-phenylethylamino)quinazoline.

5,10-Dichloro-2,3-dihydro-3-methylimidazo[1,2-c]quinazoline, m.p. 155°-157° C., from 2,5-dichloro-4-(2-hydroxy-2-methylethylamino)quinazoline.

5-Chloro-2,3-dihydro-10-trifluoromethylimidazo[1,2-c]quinazoline, m.p. 208°-212° C., from 2-chloro-4-(2-hydroxyethylamino)-5-trifluoromethylquinazoline.

5-Chloro-2,3-dihydro-10-methoxyimidazo[1,2-c]quinazoline, m.p. 212°-220° C., from 2-chloro-4-(2-hydroxyethylamino)-5-methoxyquinazoline.

5,9-Dichloro-2,3-dihydroimidazo[1,2-c]quinazoline, m.p. 210°-214° C., from 2,6-dichloro-4-(2-hydroxyethylamino)quinazoline.

EXAMPLE 7

5-Chloro-2,3-dihydro-9-fluoroimidazo[1,2-c]quinazoline

A suspension of 2-chloro-6-fluoro-4-(2-hydroxyethylamino)quinazoline (7.0 g, 29 mmol) in dichloromethane (140 ml) was heated at reflux for 4 hours with thionyl chloride (4.2 ml, 58 mmol) and triethylamine (8 ml, 58 mmol). The cooled mixture was evaporated to dryness and extracted with water (80 ml). The acidic water solution was neutralized with 25% aqueous ammonia (approx. 7 ml) and the resulting precipitate was filtered off and dried to give the title compound as light yellow crystals, m.p. 209°-211° C.

EXAMPLE 8

5-Chloroimidazo[1,2-c]quinazoline

Method A

A mixture of 5-chloro-2,3-dihydroimidazo[1,2-c]quinazoline (1.0 g, 4.9 mmol), chloranil (2.4 g, 9.7 mmol) and o-xylene (100 ml) was stirred at 150° C. for 2 h, cooled to room temperature and filtered. The filtrate was evaporated and the residue extracted with dichloromethane (25 ml). Removal of the dichloromethane left the crude title compound as an oily substance, which was purified on a silica column eluated with dichloromethane-acetone (4:1). Colourless crystals, m.p. 152°-56° C.

Method B

4-Amino-2-chloroquinazoline (3.75 g, 21 mmol) was added gradually at room temperature to a solution of bromoacetaldehyde diethyl acetal (3.6 ml, 23 mmol) in dry dimethylformamide. The resulting solution was kept at 100° C. for 5 h. The solvent was removed and the residue was triturated with dichloromethane (100 ml) and filtered. The filtrate was extracted with 1M hydrochloric acid (10 ml) and dried over sodium sulfate and charcoal. The solvent was evaporated and the residue treated with ether (10 ml) giving the title compound as a crystalline precipitate, which was filtered off, m.p. 152°-55° C.

Method C

A mixture of 5-chloro-2,3-dihydroimidazo[1,2-c]quinazoline (1.0 g, 4.9 mmol), nickel peroxide (8 g) and benzene (75 ml) was heated at reflux for 4 hours, cooled slightly, and filtered. The filtrate was evaporated to give the title compound as white crystals, m.p. 151-154.

In a similar manner the following compounds were prepared:

5-Chloro-10-trifluoromethylimidazo[1,2-c]quinazoline, m.p. 164°-167° C., from 5-chloro-2,3-dihydro-10-trifluoromethylimidazo[1,2-c]quinazoline.

10-Bromo-5-chloroimidazo[1,2-c]quinazoline, m.p. 163°-165° C., from 10-bromo-5-chloro-2,3-dihydroimidazo[1,2-c]quinazoline.

5,10-Dichloroimidazo[1,2-c]quinazoline, m.p. 184°-186° C., from 5,10-dichloro-2,3-dihydroimidazo[1,2-c]quinazoline.

5-Chloro-9-fluoroimidazo[1,2-c]quinazoline, m.p. 211°-214° C. (sinters about 207°-208° C.), from 5-chloro-9-fluoro-2,3-dihydroimidazo[1,2-c]quinazoline.

EXAMPLE 9

5-Bromo-2-chloro-4-(2-hydroxyethylamino)quinazoline

To a stirred mixture of 5-bromo-2,4-dichloroquinazoline (2.3 g, 8.2 mmol) and triethylamine (1.5 ml, 11 mmol) in dichloromethane (100 ml) was added ethanolamine (0.64 ml, 11 mmol), and the mixture was stirred for 30 min. The solvent was evaporated and the residue treated with a mixture of water (30 ml) and ether (20 ml) giving the title compound as a crystalline precipitate which was collected by filtration and dried, m.p. 165°-67° C.

In the same manner the following compounds were obtained:

2,5-Dichloro-4-(2-hydroxyethylamino)quinazoline, m.p. 169°-73° C., from 2,4,5-trichloroquinazoline.

2-Chloro-4-(2-hydroxyethylamino)quinazoline, m.p. 164°-165° C., from 2,4-dichloroquinazoline 2-Chloro-4-(3-hydroxypropylamino)quinazoline, m.p. 106°-109° C., from 2,4-dichloroquinazoline and 3-aminopropanol.

2-Chloro-4-(2-hydroxyethylamino)-5-trifluoromethylquinazoline, m.p. 153°-155° C., from 2,4-dichloro-5-trifluoromethylquinazoline.

2-Chloro-4-(2-hydroxyethylamino)-5-methoxyquinazoline, m.p. 176°-178° C., from 2,4-dichloro-5-methoxyquinazoline.

2-Chloro-6-fluoro-4-(2-hydroxyethylamino)quinazoline, m.p. 147°-150° C., from 2,4-dichloro-6-fluoroquinazoline.

2,6-Dichloro-4-(2-hydroxyethylamino)quinazoline, m.p. 152°-154° C., from 2,4,6-trichloroquinazoline.

2,5-Dichloro-4-(2-hydroxy-2-phenylethylamino)-quinazoline, m.p. 89°-93° C., from 2,4,5-trichloroquinazoline and 2-amino-1-phenyl-ethanol.

S-2,5-dichloro-4-(2-hydroxy-1-methylethylamino)-quinazoline, m.p. 175°-178° C., from 2,4,5-trichloroquinazoline and S(+)-2-amino-1-propanol.

R-2,5-dichloro-4-(2-hydroxy-1-methylethylamino)-quinazoline, m.p. 180°-182° C., from 2,4,5-trichloroquinazoline and R(−)-2-amino-1-propanol.

2,5-Dichloro-4-(2-hydroxy-2-methylethylamino)-quinazoline, m.p. 101°-104° C., from 2,4,5-trichloroquinazoline and 1-amino-2-propanol.

2,5-Dichloro-4-(1,1-dimethyl-2-hydroxyethylamino)-quinazoline, m.p. 147°-150° C., from 2,4,5-trichloroquinazoline and 2-amino-2-methyl-1-propanol.

EXAMPLE 10

5-(3-Cyclopropyl-1,2,4-oxadiazol-5-yl)-2,3-dihydrodiimidazo[1,5-a:1',2'-c]quinazoline A mixture of ethyl 2,3-dihydrodiimidazo[1,5-a:1',2'-c]quinazoline-5-carboxylate (1.0 g, 3.5 mmol), cyclopropancarboxamide oxime (1.0 g, 10 mmol), crushed 4 Å molecular sieves (1 g), and sodium hydride (approx. 10 mg of a 55% oil dispersion) in dry DMF was stirred at room temperature for one week. Additional catalytic amounts of NaH were added regularly during the reaction (4×10 mg). Then dichloromethane (50 ml) was added, and the insoluble material was removed by filtration through celite. The filtrate was evaporated in vacuo, the residue triturated with water (50 ml), and the resulting precipitate was filtered off. The crude product thus obtained was heated at reflux for 10 min. in a mixture of water (10 ml), ethanol (5 ml), and 4M sodium hydroxide (2 ml). Then the mixture was cooled to room temperature and the precipitate was filtered off and dried to give the title compound, m.p. 235°-238° C. (Compound 2).

EXAMPLE 11

5-(5-Cyclopropyl-1,2,4-oxadiazol-3-yl)-2,3-dihydro-12-isopropoxydiimidazo[1,5-a:1',2'-c]quinazoline Sodium (30 mg, 1.3 mmol) was dissolved in 20 ml of dry isopropyl alcohol. 5-(5-Cyclopropyl-1,2,4-oxadiazol-3-yl)-12-fluoro-2,3-dihydrodiimidazo[1,5-a:1',2'-c]quinazoline (0.2 g, 0.6 mmol) was added and the mixture was heated at reflux for 10 min. Then the solvent was evaporated in vacuo and the residue was triturated with 25 ml of water. The insoluble material was filtered off and dried to give the title compound as pale crystals, m.p. 211°-214° C. Yield 0.17 g (75%). (Compound 43).

In a similar manner the following compounds were prepared:

5-(5-Cyclopropyl-1,2,4-oxadiazol-3-yl)-2,3-dihydro-12-(2-dimethylaminoethoxy)diimidazo[1,5-a:1',2'-c]quinazoline, by reaction of 5-(5-cyclopropyl-1,2,4-oxadiazol-3-yl)-12-fluoro-2,3-dihydrodiimidazo[1,5-a:1',2'-c]quinazoline with 2-dimethylaminoethanol. (Compound 44).

5-(5-Cyclopropyl-1,2,4-oxadiazol-3-yl)-12-(2-fluoro-phenoxy)-2,3-dihydrodiimidazo[1,5-a:1',2'-c]quinazoline, m.p. 212°–215° C., from 5-(5-cyclopropyl-1,2,4-oxadiazol-3-yl)-12-fluoro-2,3-dihydrodiimidazo[1,5-a:1',2'-c]quinazoline and 2-fluorophenol in DMF. (Compound 45).

EXAMPLE 12

5-(3-Cyclopropyl-1,2,4-oxadiazol-5-yl)-2,3-dihydro-12-morpholinodiimidazo[1,5-a:1',2'-c]quinazoline A solution of 5-(3-cyclopropyl-1,2,4-oxadiazol-5-yl)-12-fluoro-2,3-dihydrodiimidazo[1,5-a:1',2'-c]quinazoline (0.25 g, 0.7 mmol) in a mixture of morpholine (10 ml) and DMF (15 ml) was heated at 120° C. for 6 h. Then the solvent was evaporated and the solid residue was triturated with 10 ml of water, filtered off and dried to give the title compound as pale crystals, m.p. 217°–220° C. Yield 0.16 g (57%). (Compound 46).

EXAMPLE 13

5-(5-Cyclopropyl-1,2,4-oxadiazol-3-yl)-2,3-dihydro-12-dimethylaminodiimidazo[1,5-a:1',2'-c]quinazoline Dimethylamine was bubbled through a stirred suspension of 5-(5-cyclopropyl-1,2,4-oxadiazol-3-yl)-12-fluoro-2,3-dihydrodiimidazo[1,5-a:1',2'-c]quinazoline (1.0 g, 3 mmol) in dry DMF (25 ml) for 5 min. at ambient temperature. Again after 2 h dimethylamine was passed through the reaction mixture for 5 min. and stirring was continued for one more hour. The resulting solution was evaporated in vacuo and the residue was treated with 4 ml of 1M NaOH and 20 ml of water. The insoluble material was filtered off, rinsed on the filter until the wash water was no longer basic, and dried. Recrystallization from isopropyl alcohol gave the title compound as pale yellow crystals, m.p. 148°–150° C. Yield 0.50 g (47%). (Compound 47).

EXAMPLE 14

5-Chloro-10-fluoro-2,3-dihydroimidazo[1,2-c]quinazoline

A stirred mixture of 10 fluoro-2,3,5,6-tetrahydro-5-oxoimidazo[1,2-c]quinazoline (1.45 g, 7 mmol), tripropylamine (5.4 ml, 7 mmol), and phosphorus oxychloride (2.7 ml) was heated at 140° C. for 45 min. The hot solution was then poured with virogous stirring into 200 ml of crushed ice and water and stirred until a homogeneous slurry was obtained. The mixture was filtered, and the acidic filtrate was neutralized with 25% aqueous ammonia and the resulting precipitate was filtered off and dried to give the title compound as tan crystals, m.p. 281°–285° C. Yield 1.2 g (76%).

In the same way, 2,5-dichloro-10-fluoro-imidazo[1,2-c]quinazoline was prepared from 10-fluoro-2,3,5,6-tetrahydro-2,5-dioxoimidazo[1,2-c]quinazoline.

EXAMPLE 15

2,3-Dihydro-5-(5-trifluoromethyl-1,2,4-oxadiazol-3-yl)diimidazo[1,5-a:1',2'-c]quinazoline Trifluoroacetic anhydride (TFAA, 2 g) was added to a stirred suspension of 2,3-dihydrodiimidazo[1,5-a:1',2'-c]quinazoline-5-carboxamide oxime (2.5 g, 9 mmol). With 3 h intervals, two additional 1 g portions of TFAA was added, and stirring was continued overnight. The solvent was removed in vacuo and the residue was purified on a silica column using ethyl acetate as eluent.

The title compound was obtained as pale crystals, m.p. 220°–224° C. (Compound 48).

EXAMPLE 16

2,3-Dihydrodiimidazo[1,5-a:1',2'-c]quinazoline-5-carboxamide oxime

A mixture of 5-cyano-2,3-dihydrodiimidazo[1,5-a:1',2']quinazoline (3 g, 13 mmol), hydroxylamine hydrochloride (1.4 g, 20 mmol), potassium carbonate (3.4 g, 25 mmol) water (2 ml), and ethanol (40 ml), was stirred at 80° C. for 3 h and then cooled to 0° C. and filtered. The filter cake was rinsed with 30 ml of water and dried, giving 2.7 g (78%) of the title compound, m.p. 209°–212° C.

EXAMPLE 17

5-Cyano-2,3-dihydrodiimidazo[1,5-a:1',2'-c]quinazoline

A mixture of 2,3-dihydrodiimidazo[1,5-a:1',2'-c]quinazoline-5-carboxamide (1 g, 4 mmol) (prepared by standard methods from the corresponding carboxylic acid ethyl ester, Compound 3) and phosphorus pentachloride (0.9 g, 4.1 mmol) in phosphorus oxychloride (10 ml) was stirred at reflux for 3 h, and then evaporated to dryness. The residue was partitioned between 25 ml of water and 25 ml of dichloromethane. The organic layer was extracted with 4×25 ml of 10% acetic acid. The combined aqueous phases were adjusted to pH around 11 and cooled to 0° C. The precipitate which had formed was filtered off and dried, giving the title compound as yellow crystals, m.p. 227°–240° C. (decomposition). Yield 0.53 g (57%). (Compound 49).

We claim:

1. A compound of formula I:

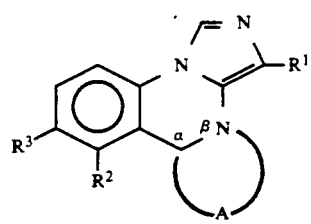

wherein

A together with the α-marked carbon atom and the β-marked nitrogen atom is one of the groups

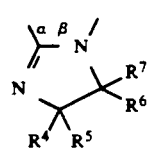   a

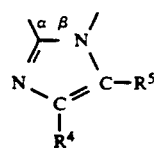   b

-continued

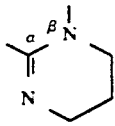

wherein R⁴, R⁵, R⁶ and R⁷ independently are hydrogen, halogen, C₁₋₆-alkyl or phenyl;
R¹ is

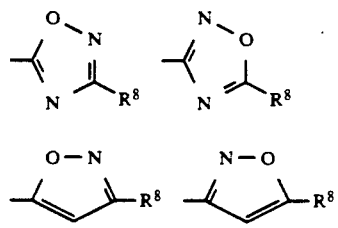

CN or CO₂R⁸, wherein R⁸ is hydrogen, C₁₋₆-alkyl, C₃₋₇-cycloalkyl, trifluoromethyl or C₁₋₆-alkoxymethyl; and R² and R³ independently are hydrogen, halogen, CN, C₁₋₆-alkyl, C₂₋₆-alkenyl, C₂₋₆-alkynyl, trifluoromethyl, C₁₋₆-alkoxy, dimethylaminoethoxy, morpholino, phenoxy optionally substituted with halogen, or NR⁹R¹⁰, wherein R⁹ and R¹⁰ independently are hydrogen or C₁₋₆-alkyl; or a pharmaceutically acceptable salt thereof.

2. A compound which is 5-(5-cyclopropyl-1,2,4-oxadiazol-3-yl)-2,3-dihydrodiimidazo[1,5-a:1',2'-c]quinazoline.

3. A compound which is 12-chloro-5-(5-cyclopropyl-1,2,4-oxadiazol-3-yl)-2,3-dihydrodiimidazo[1,5-a:1',2'-c]quinazoline.

4. A compound which is 12-bromo-5-(5-cyclopropyl-1,2,4-oxadiazol-3-yl)-2,3-dihydrodiimidazo[1,5-a:1',2'-c]quinazoline.

5. A compound which is 12-bromo-5-(3-cyclopropyl-1,2,4-oxadiazol-5-yl)-2,3-dihydrodiimidazo[1,5-a:1',2'-c]quinazoline.

6. A compound which is 5-(5-cyclopropyl-1,2,4-oxadiazol-3-yl)-11-fluoro-2,3-dihydrodiimidazo[1,5-a:1',2'-c]quinazoline.

7. A pharmaceutical composition for use in the treatment of a central nervous system ailment comprising an effective amount of a compound according to claim 1 together with a pharmaceutically-acceptable carrier or diluent.

8. A pharmaceutical composition according to claim 7 in the form of an oral dosage unit containing 0.1-100 mg of the active compound.

9. A method of treating a central nervous system ailment in a subject in need of such treatment comprising administering to said subject a pharmaceutical composition comprising an effective amount of a compound of formula I

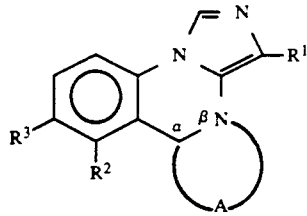

wherein
A together with the α-marked carbon atom and the β-marked nitrogen atom is one of the groups

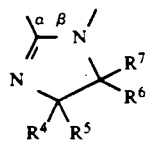

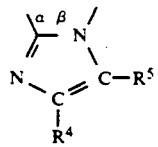

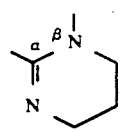

wherein R⁴, R⁵, R⁶ and R⁷ independently are hydrogen, halogen, C₁₋₆-alkyl or phenyl;
R¹ is

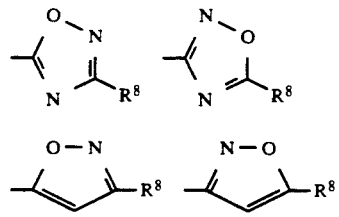

CN or CO₂R⁸, wherein R⁸ is hydrogen, C₁₋₆-alkyl, C₃₋₇-cycloalkyl, trifluoromethyl or C₁₋₆-alkoxymethyl; and R² and R³ independently are hydrogen, halogen, CN, C₁₋₆-alkyl, C₂₋₆-alkenyl, C₂₋₆-alkynyl, trifluoromethyl, C₁₋₆-alkoxy, dimethylaminoethoxy, morpholino, phenoxy optionally substituted with halogen, or NR⁹R¹⁰, wherein R⁹ and R¹⁰ independently are hydrogen or C₁₋₆-alkyl; together with a pharmaceutically acceptable carrier or diluent.

10. The method according to claim 9, wherein the pharmaceutical composition acts as an anticonvulsant, anxiolytic, hypnotic, antipsychotic or antiemetic, or stimulates the cognitive function of the brain of the subject.

* * * * *